United States Patent
Shin et al.

(10) Patent No.: US 9,636,392 B2
(45) Date of Patent: May 2, 2017

(54) PRODUCTION METHOD FOR CAPSULAR POLYSACCHARIDE HAVING PNEUMOCOCCAL SEROTYPE

(71) Applicant: SK CHEMICALS CO., LTD., Seongnam-si, Gyeonggi-do (KR)

(72) Inventors: Jin-Hwan Shin, Seoul (KR); Mahn-Hoon Park, Yongin-si (KR); Hun Kim, Suwon-si (KR); Myeong-Ju Noh, Seoul (KR); Su-Jin Park, Seongnam-si (KR)

(73) Assignee: SK CHEMICAL CO., LTD., Gyeonggi-Do (KR)

( * ) Notice: Subject to any disclaimer, the term of this patent is extended or adjusted under 35 U.S.C. 154(b) by 0 days.

(21) Appl. No.: 14/426,585

(22) PCT Filed: Sep. 6, 2013

(86) PCT No.: PCT/KR2013/008048
§ 371 (c)(1),
(2) Date: Mar. 6, 2015

(87) PCT Pub. No.: WO2014/038879
PCT Pub. Date: Mar. 13, 2014

(65) Prior Publication Data
US 2015/0231225 A1    Aug. 20, 2015

(30) Foreign Application Priority Data
Sep. 7, 2012 (KR) .................. 10-2012-0099348

(51) Int. Cl.
*C12P 19/04* (2006.01)
*A61K 39/09* (2006.01)

(52) U.S. Cl.
CPC ............ *A61K 39/092* (2013.01); *C12P 19/04* (2013.01)

(58) Field of Classification Search
None
See application file for complete search history.

(56) References Cited

U.S. PATENT DOCUMENTS

| | | |
|---|---|---|
| 5,847,112 A | 12/1998 | Kniskern et al. |
| 2006/0228381 A1 | 10/2006 | Bahler et al. |
| 2008/0102498 A1 | 5/2008 | Bahler et al. |
| 2008/0286838 A1 | 11/2008 | Yuan et al. |
| 2010/0158953 A1 | 6/2010 | Crinean |

FOREIGN PATENT DOCUMENTS

| | | |
|---|---|---|
| CN | 101155833 A | 4/2008 |
| CN | 101180079 Y | 5/2008 |
| CN | 101663327 A | 3/2010 |
| KR | 20100030729 A | 3/2010 |
| RU | 2009 112 453 A | 11/2010 |
| WO | WO 2006/110352 A2 | 10/2006 |
| WO | WO 2006/110381 A1 | 10/2006 |
| WO | WO 2008/118752 A2 | 10/2008 |
| WO | WO 2011/151841 A1 | 12/2011 |

OTHER PUBLICATIONS

International Search Report (PCT/ISA/210) mailed on Nov. 26, 2013, by the Korean Patent Office as the International Searching Authority for International Application No. PCT/KR2013/008048.
Written Opinion (PCT/ISA/237) mailed on Nov. 26, 2013, by the Korean Patent Office as the International Searching Authority for International Application No. PCT/KR2013/008048.
Leal et al., "Investigation of Cultivation Conditions for Capsular Polysaccharide Production by *Streptococcus pneumoniae* Serotype 14," Electronic Journal of Biotechnology, (2011), vol. 14, No. 5, pp. 1-7.
Office Action (Inquiry) issued on Jun. 3, 2016, by the Patent Office of the Russian Federation in corresponding Russian Patent Application No. 2015109997/10, and an English Translation of the Office Action. (10 pages).
Massaldi, Hugo et al. "Features of bacterial growth polysaccharide production of *Streptococcus pneumoniae* serotype 14" Biontechnol. Appl. Niochem (2010) vol. 55, pp. 37-43 (7 pages).
Extended European Search Report issued Mar. 29, 2016, by the European Patent Office in corresponding European Application No. 13834636.6 (7 pages).
First Office Action issued by the State of Intellectual Property Office of the People's Republic of China on Feb. 4, 2017 in corresponding Chinese Application No. 2013800580195 (7 pages).

*Primary Examiner* — Jennifer Graser
(74) *Attorney, Agent, or Firm* — Buchanan Ingersoll & Rooney

(57) ABSTRACT

The present invention provides an improved method of producing a capsular polysaccharide having a pneumococcal serotype. The method according to the present invention includes a step of additionally culturing bacterial cells producing a pneumococcal serotype without pH adjustment, thereby removing a protein precipitation process by acidification with a pH adjuster.

13 Claims, 6 Drawing Sheets

PRODUCTION METHOD FOR CAPSULAR POLYSACCHARIDE HAVING PNEUMOCOCCAL SEROTYPE

TECHNICAL FIELD

The present invention relates to a method of producing a capsular polysaccharide having a pneumococcal serotype, and more particularly, to a method of producing a capsular polysaccharide having a pneumococcal serotype by removing impurities such as proteins and nucleic acids from a culture broth of bacterial cells producing the pneumococcal serotype.

BACKGROUND ART

Pneumococcus (*Streptococcus pneumoniae*) is a Gram-positive bacterium belonging to the family Streptococcaceae, within the order Lactobacillus, and it causes diseases such as pneumonia, bacteremia, otitis media, and meningitis in humans. Cells of pneumococcal serotypes have a capsule which is a polysaccharide coating surrounding each cell. This capsule interferes with phagocytosis by preventing antibodies from attaching to the bacterial cells. The cells have been categorized into over 90 serotypes based on immunological characteristics, some of which are reported to cause invasive diseases. A total of 37 serotypes were identified from invasive *Streptococcus pneumoniae* collected from 1996 to 2008, and the main serotypes, 19F>23F>19A>6A>3>9V>6B frequent in this order, account for a majority of 53.4%. Capsular polysaccharides of these pneumococcal serotypes have been used in the production of vaccines such as polysaccharide vaccines and polysaccharide-protein conjugate vaccines.

Capsular polysaccharides used in the production of polysaccharide vaccines and polysaccharide-protein conjugate vaccines are obtained from culture broths of bacterial cells producing respective serotypes. Each strain is cultured under optimal temperature, pH and agitation until it reaches a maximum density. To obtain pneumococcal capsular polysaccharides that are not secreted outside the cytoplasm, cell lysis is carried out using a lysing agent such as sodium deoxycholate (DOC). When cells are lysed, various proteins and nucleic acids of the strain are released, together with capsular polysaccharides, and they must be removed by a post-culture purification process. To minimize the risk of adverse events by any substance other than an antigen after vaccination, there are strict specifications for protein and nucleic acid contents. For instance, in the case of Prevnar 7™, protein and nucleic acid contents in each serotype satisfy the specifications of 2-5% or less and 1-2% or less on a dry weight basis, respectively.

International Patent Publication No. WO 2006/110352 discloses a method of producing capsular polysaccharides comprising cultivating of *Streptococcus pneumonia*, cell lysis, protein precipitation by acidification of the cell lysate to a pH of less than 5.5, incubation without agitation, and centrifugation and/or filtration. Further, International Patent Publication No. WO 2008/118752 discloses a method of producing capsular polysaccharides by performing ultrafiltration and diafiltration of a cell lysate followed by a protein precipitation process by acidification. However, all these related production methods require the protein precipitation process by acidification with a pH adjuster, which makes the overall process complicated and also causes modification of capsular polysaccharide and generation of harmful substances.

DETAILED DESCRIPTION OF THE INVENTIVE CONCEPT

Technical Problem

The inventors have conducted various studies in order to improve a method of producing a capsular polysaccharide having a pneumococcal serotype. Surprisingly, the inventors found that pH may be lowered to a range suitable for protein precipitation, namely, to pH of 5.5 or lower by products from cultivating (especially, lactic acid, etc.), when an additional cultivating is performed under the same conditions without pH adjustment. That is, the inventors found that the protein precipitation process through acidification with a pH adjuster may be removed by performing an additional cultivating without pH adjustment and then performing cell lysis and the protein precipitation process.

Accordingly, the objective of the present invention is to provide an improved method of producing a capsular polysaccharide having a pneumococcal serotype.

Technical Solution

According to an aspect of the present invention, there is provided a method of producing a capsular polysaccharide having a pneumococcal serotype, comprising the following steps of:

(a) cultivating bacterial cells that produce a pneumococcal serotype, while maintaining pH of a culture broth in the range of 7.0 to 9.4;

(b) terminating the cultivating of step (a) at a time between when the absorbance of the culture broth remains constant and when the absorbance begins to decrease;

(c) performing additional cultivating of the culture broth obtained from step (b) without pH adjustment until the pH of the culture broth reaches pH of 5.5 or lower;

(d) adding a lysing agent to the culture broth obtained from step (c) to lyse cells, precipitating proteins, and removing the precipitated proteins and cell debris to obtain a clarified cell lysate; and (e) isolating and purifying the capsular polysaccharide from the lysate obtained from step (d).

In the production method of the present invention, the pneumococcal serotype may be 1, 2, 3, 4, 5, 6A, 6B, 7F, 9N, 9V, 14, 18C, 19A, 19F, 22F, 23F or 33F.

The cultivating of step (a) may be performed at 34-38° C. under agitation at 50-150 rpm.

In an embodiment of the present invention, step (b) may be performed by terminating the cultivating of step (a) within 1 to 3 hours from the time when absorbance of the culture broth remains constant.

The additional cultivating of step (c) may be performed at 34-38° C. under agitation at 50-150 rpm without pH adjustment.

The lysing agent used in step (d) may be sodium deoxycholate. In another embodiment of the present invention, step (d) may be performed by adding the lysing agent to the culture broth obtained from step (c) to lyse cells, then incubating the resulting cell lysate at 10-20° C. for 3-24 hours without agitation to precipitate proteins, and removing the precipitated proteins and cell debris by centrifugation.

In still another embodiment of the present invention, the isolating and purifying of step (e) may include the following steps:

(i) filtering the lysate obtained from step (d) using a depth filter;

(ii) concentrating a filtrate obtained from step (i), followed by ultrafiltration and centrifugation;

(iii) reacting the supernatant obtained from step (ii) with a cationic surfactant, and then centrifuging the obtained solution to produce a pellet or supernatant containing capsular polysaccharides;

(iv) reacting the capsular polysaccharides obtained from step (iii) with sodium iodide, followed by centrifugation, thereby obtaining the supernatant;

(v) adding activated carbon to the solution obtained from step (iv), followed by filtration; and (vi) concentrating a filtrate obtained from step (v), followed by ultrafiltration and centrifugation, thereby obtaining capsular polysaccharides.

In the above embodiment, concentrating of step (ii) may be performed using a 100 kDa membrane, and concentrating of step (vi) may be performed using a 30 kDa membrane. Further, the cationic surfactant used in step (iii) may be cetyltrimethylammonium bromide, and cetyltrimethylammonium bromide may be used at a concentration of 0.5~3.0%. In addition, the activated carbon used in step (v) may be used at a concentration of 1~5% (w/v).

Advantageous Effects

In a production method according to the present invention, a pH adjuster for protein precipitation is not used. That is, the present invention demonstrated that when additional cultivating of bacterial cells producing a pneumococcal serotype is performed under the same conditions without pH adjustment, the pH may be lowered to a range suitable for protein precipitation, namely, to pH of 5.5 or lower by products from the culturing (especially, lactic acid, etc.). Therefore, the production method of the present invention does not require use of the pH adjuster for protein precipitation, thereby minimizing modification of capsular polysaccharides and generation of any harmful substances and simplifying the production process. The capsular polysaccharide having the pneumococcal serotype obtained by the production method of the present invention may be advantageously used to produce polysaccharide vaccines and polysaccharide-protein conjugate vaccines.

BEST MODE

Figure 1:
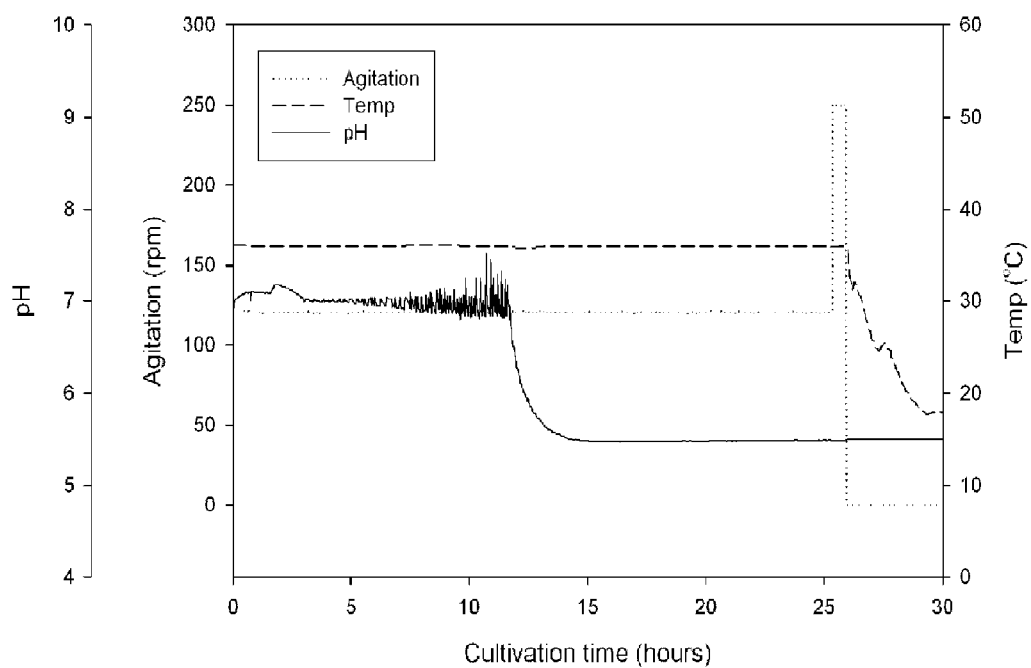
FIG. 1 shows changes in pH in culture broth and conditions for cultivating bacterial cells producing the pneumococcal serotype 3.
Figure 2:
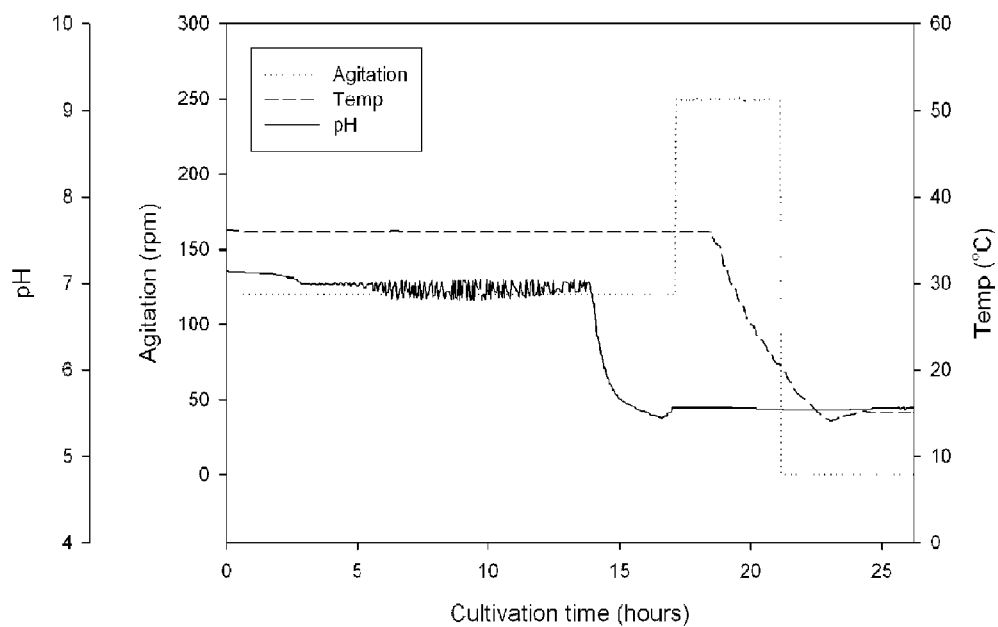
FIG. 2 shows changes in pH in culture broth and conditions for cultivating bacterial cells producing the pneumococcal serotype 6B.
Figure 3:
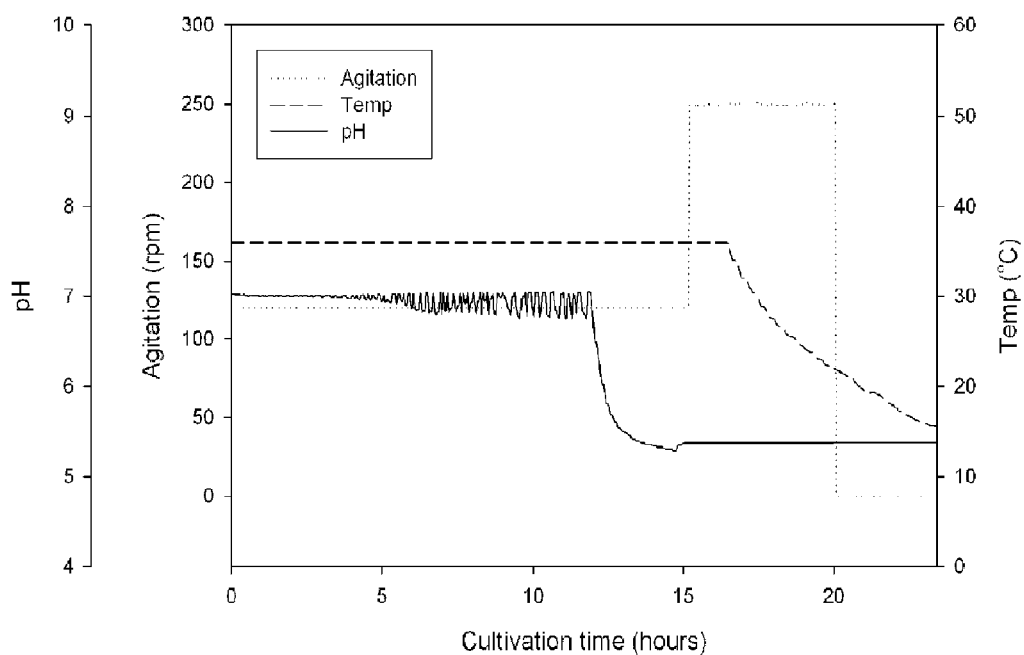
FIG. 3 shows changes in pH in culture broth and conditions for cultivating bacterial cells producing the pneumococcal serotype 7F.
Figure 4:
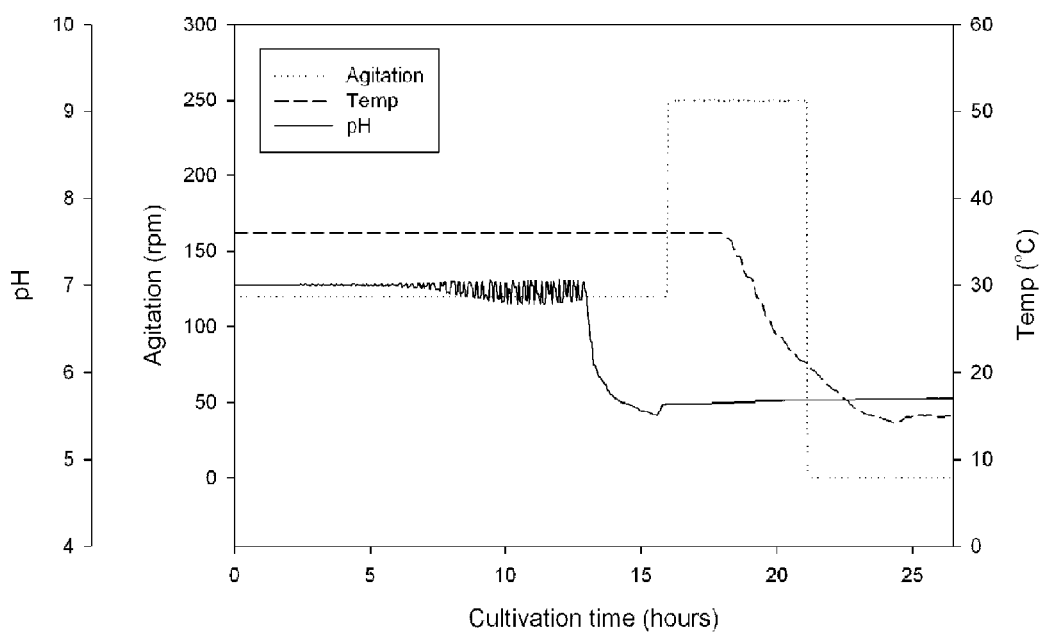
FIG. 4 shows changes in pH in culture broth and conditions for cultivating bacterial cells producing the pneumococcal serotype 14.
Figure 5:
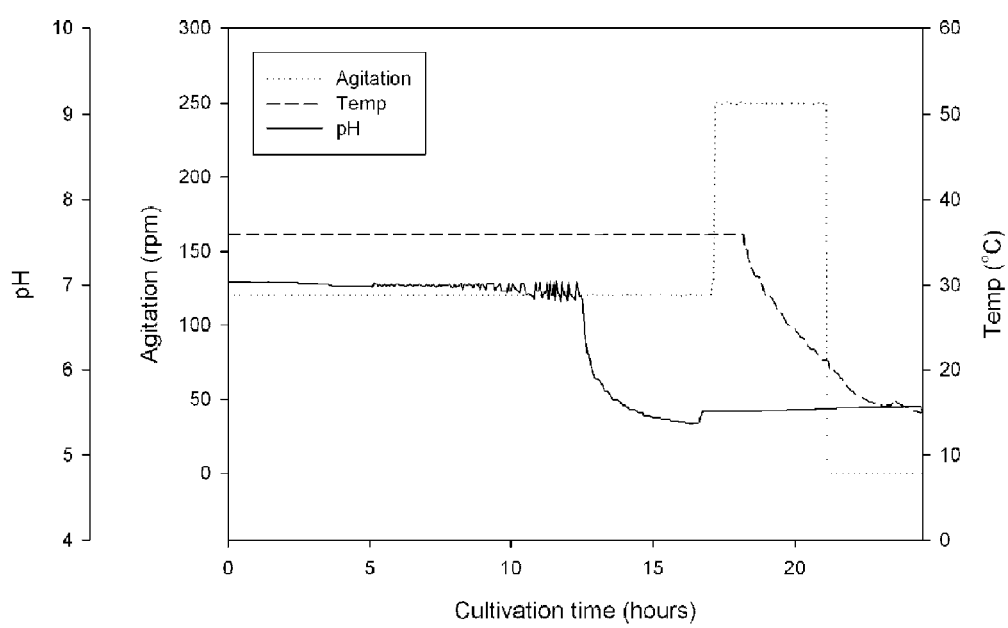
FIG. 5 shows changes in pH in culture broth and conditions for cultivating bacterial cells producing the pneumococcal serotype 19A.
Figure 6:
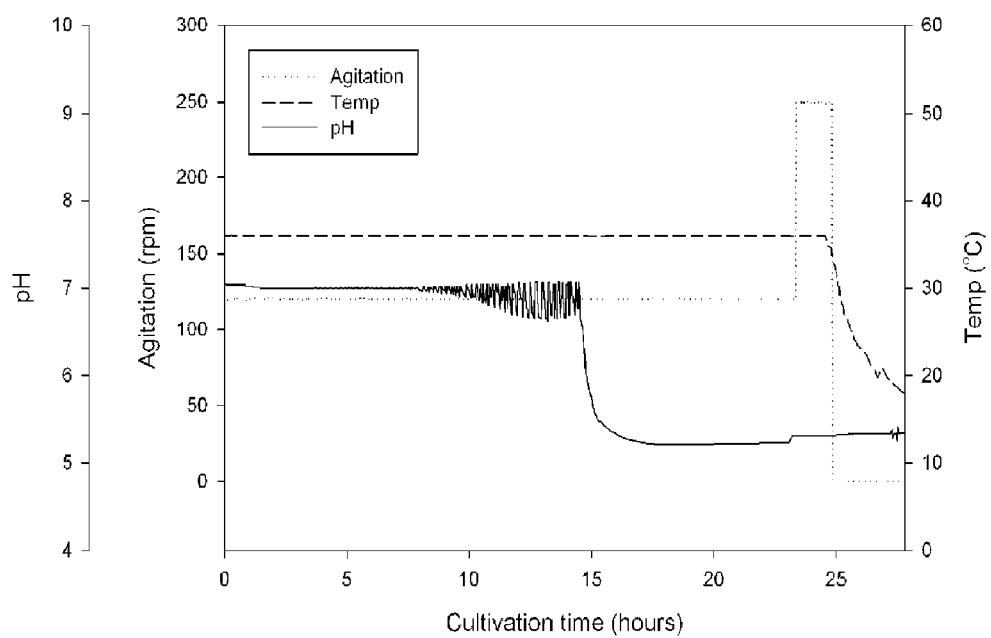
FIG. 6 shows changes in pH in culture broth and conditions for cultivating bacterial cells producing the pneumococcal serotype 23F.

The present invention provides a method of producing a capsular polysaccharide having a pneumococcal serotype, including the following steps:

(a) cultivating bacterial cells that produce a pneumococcal serotype, while maintaining pH of a culture broth in the range of 7.0 to 9.4;

(b) terminating the cultivating of step (a) at a time between when the absorbance of the culture broth remains constant and when the absorbance begins to decrease;

(c) performing additional cultivating of the culture broth obtained from step (b) without pH adjustment until the pH of the culture broth reaches pH of 5.5 or lower;

(d) adding a lysing agent to the culture broth obtained from step (c) to lyse cells, precipitating proteins, and removing the precipitated proteins and cell debris to obtain a clarified cell lysate; and (e) isolating and purifying the capsular polysaccharide from the lysate obtained from step (d).

In step (a) of the production method according to the present invention, the pneumococcal serotype may be any kind of serotype that is used in production of pneumococcal vaccines; for example, the serotypes may include the serotype 1, 2, 3, 4, 5, 6A, 6B, 7F, 9N, 9V, 14, 18C, 19A, 19F, 22F, 23F, and 33F, but are not limited thereto. The bacterial cells producing the pneumococcal serotype are known in the art, and any known bacterial cell may be used without any limitation (e.g., see WO 2006/110381). The cultivating of step (a) of the production method according to the present invention may be performed in a general medium such as a soy-based medium, while maintaining pH of the culture broth in the range of 7.0 to 9.4, preferably, of 7.2 to 8.2 by using, for example, sodium hydroxide. The cultivation may be performed under any known culture conditions, for example, at 34-38° C. under agitation at 50-150 rpm. pH conditions suitable for seed culture and main culture for production of representative serotypes of *Streptococcus pneumoniae* are given in the following Table 1.

TABLE 1 pH condition for each serotype

| Serotype | Seed culture condition | Main culture condition |
|---|---|---|
| 1 | pH 7.2 ± 0.2 | pH 7.2 ± 0.2 |
| 2 | pH 7.2 ± 0.2 | pH 7.2 ± 0.2 |
| 3 | pH 7.2 ± 0.2 | pH 7.2 ± 0.2 |
| 4 | pH 7.6 ± 0.6 | pH 7.6 ± 0.6 |
| 5 | pH 7.2 ± 0.2 | pH 7.2 ± 0.2 |
| 6A | pH 7.2 ± 0.2 | pH 7.2 ± 0.2 |
| 6B | pH 7.2 ± 0.2 | pH 7.2 ± 0.2 |
| 7F | pH 7.2 ± 0.2 | pH 7.2 ± 0.2 |
| 9N | pH 7.6 ± 0.6 | pH 7.6 ± 0.6 |
| 9V | pH 7.6 ± 0.6 | pH 7.6 ± 0.6 |
| 14 | pH 7.6 ± 0.6 | pH 7.6 ± 0.6 |
| 18C | pH 7.2 ± 0.2 | pH 7.2 ± 0.2 |
| 19A | pH 7.2 ± 0.2 | pH 7.2 ± 0.2 |
| 19F | pH 7.2 ± 0.2 | pH 7.2 ± 0.2 |
| 22F | pH 7.2 ± 0.2 | pH 7.2 ± 0.2 |
| 23F | pH 7.2 ± 0.2 | pH 7.2 ± 0.2 |
| 33F | pH 7.2 ± 0.2 | pH 7.2 ± 0.2 |

The production method according to the present invention does not require use of a pH adjuster for protein precipitation. That is, the present inventors surprisingly found that pH may be lowered to a range suitable for protein precipitation, namely, to pH of 5.5 or lower by products from cultivation (especially, lactic acid, etc.), when an additional cultivating is performed under the same conditions without pH adjustment. Therefore, the production method of the present invention includes performing the additional cultivating without pH adjustment after culturing bacterial cells that produce the pneumococcal serotype, preferably, at the time point when the bacterial cells reach a maximum growth, and then performing cell lysis and protein precipitation processes. Thus, the production method of the present invention does not require use of a pH adjuster for protein precipitation, thereby minimizing modification of capsular polysaccharide and generation of any harmful substances and simplifying the production process.

The production method of the present invention, therefore, includes the step of terminating the cultivating of step (a) at a time between when the absorbance of the culture broth remains constant and when the absorbance begins to decrease [i.e., step (b)]; and the step of performing additional cultivating the culture broth obtained from step (b) without pH adjustment until the pH of the culture broth reaches pH of 5.5 or lower [i.e., step (c)].

As cultivation is performed according to step (a) of the production method of the present invention, the bacterial cells proliferate and absorbance [e.g., absorbance at 590 nm ($OD_{590}$)] of the culture broth gradually increases to reach the plateau (the maximum growth) and then remains constant (about 7-24 hours after starting the cultivation). Subsequently, the absorbance decreases within 1 to 3 hours. In an embodiment of the present invention, therefore, step (b) may be performed by terminating the cultivating of step (a) within 1 to 3 hours from the time when the absorbance of the culture broth remains constant. The additional cultivating of step (c) may be performed without pH adjustment under the same conditions as in step (a), that is, at 34-38° C. under agitation at 50-150 rpm. When such additional cultivating is performed, pH of the culture broth spontaneously decreases to 5.5 or lower, thereby providing a proper pH needed for protein precipitation.

The production method of the present invention includes the step of adding a lysing agent to the culture broth obtained from step (c) to lyse cells, precipitating proteins, and removing the precipitated proteins and cell debris to obtain a clarified cell lysate [i.e., step (d)].

The cell lysis may be performed in accordance with a known method, for example, a method disclosed in WO 2006/110381, WO 2008/118752, etc. For example, cell lysis may be performed using sodium deoxycholate as a lysing agent. Sodium deoxycholate may be used at a concentration of 0.10~0.15% (concentration after addition of sodium deoxycholate), but is not limited thereto. As cells are lysed, capsular polysaccharides of the pneumococcal serotype are released outside the cytoplasm. Further, protein precipitation may be performed by, for example, incubation at 10-20° C., and removal of the precipitated proteins and cell debris may be performed by a typical method (e.g., centrifugation). In an embodiment of the present invention, step (d) may be performed by adding a lysing agent to the culture broth obtained from step (c) to lyse cells, precipitating proteins by incubation of the obtained lysate at 10-20° C. for 3-24 hours without agitation, and removing the precipitated proteins and cell debris by centrifugation.

The production method of the present invention includes the step of isolating and purifying the capsular polysaccharide from the lysate by removing impurities (e.g., proteins, and nucleic acids contained in cells) from the lysate obtained from step (d) [i.e., step (e)]. The isolation and purification of the capsular polysaccharide may be performed in accordance with a known purification method, for example, a method disclosed in WO 2006/110381 and WO 2008/118752. In an embodiment, the isolation and purification of step (e) may include the following steps:

(i) filtering the lysate obtained from step (d) using a depth filter;

(ii) concentrating a filtrate obtained from step (i), followed by ultrafiltration and centrifugation;

(iii) reacting the supernatant obtained from step (ii) with a cationic surfactant, and then centrifuging the resulting solution to obtain a pellet or supernatant containing capsular polysaccharides;

(iv) reacting the capsular polysaccharides obtained from step (iii) with sodium iodide, followed by centrifugation, thereby obtaining a supernatant;

(v) adding activated carbon to the supernatant obtained from step (iv), followed by filtration; and (vi) concentrating a filtrate obtained from step (v), followed by ultrafiltration and centrifugation, thereby obtaining capsular polysaccharide.

In the above embodiment, lysates that remain even after centrifugation for the removal of the precipitated proteins and cell debris are removed by filtration using the depth filter.

Further, proteins and nucleic acids may be removed by repeating concentration/ultrafiltration twice. In an embodiment, the concentrating of step (ii) may be performed using a 100 kDa membrane, and the concentrating of step (vi) may be performed using a 30 kDa membrane. In this process, the ultrafiltration may also be referred to as 'diafiltration'.

Further, the cationic surfactant used in step (iii) may be cetyltrimethylammonium bromide. Cetyltrimethylammonium bromide (Cetrimonium Bromide, Hexadecyl-trimethylammonium bromide (HB)) may be used at a concentration of 0.5-3% (concentration after addition of cetyltrimethylammonium bromide). The used cationic surfactant such as HB may be precipitated and removed by using sodium iodide. When centrifugation is performed in step (iii), capsular polysaccharides may be present in the pellet (e.g., serotype 1, 2, 3, 4, 5, 6A, 6B, 9N, 9V, 18C, 19A, 19F, 22F, 23F, etc.) or supernatant (e.g., serotype 7F, 14, 33F, etc.). The capsular polysaccharides obtained in the form of pellet may be dissolved in a proper solvent (e.g., sodium chloride aqueous solution, etc.), and then be used in the subsequent step (i.e., reaction with sodium iodide). The capsular polysaccharides present in the supernatant may be used in the subsequent step (i.e., reaction with sodium iodide) without additional separation.

Further, activated carbon in step (v) may be preferably used at a concentration of 1~5% (w/v).

Hereinafter, the present invention will be described in more detail with reference to Examples. However, the following Examples described herein should be considered in a descriptive sense only and not for purposes of limitation.

EXAMPLE

A soy-based medium used in the following Examples has the composition as in Table 2 below.

TABLE 2

| Medium composition | Content per liter (g) |
| --- | --- |
| Soybean peptone (Soytone ™, BD 243620) | 28 |
| Sodium chloride | 3.5 |
| Potassium phosphate | 0.7 |

Example 1. Production of Capsular Polysaccharides of Pneumococcal Serotypes 3, 6B, and 19A <Preparation of Cell Bank>

Respective seed stocks producing pneumococcal serotypes 3, 6B, and 19A were obtained from American Type Culture Collection [ATCC]. Strains used in seed culture and main culture are given in the following Table 3.

TABLE 3

| Serotype | ATCC No. |
| --- | --- |
| 3 | 6303 |
| 6B | 6326 |
| 19A | 10357 |

Several generations of seed stocks were created (generations F1, F2, and F3). Two additional generations of seed stocks were produced. The first additional generation was cultured from an F3 vial, and the subsequent generation was cultured from a vial of the first additional generation. Seed vials were stored frozen (←−70° C.) with synthetic glycerol as a cryopreservative. For cell bank preparation, all cultures were grown in a soy-based medium. Prior to freezing, cells were concentrated by centrifugation, spent medium was removed, and cell pellets were re-suspended in a fresh medium containing a cryopreservative (e.g., synthetic glycerol).

<Culture and Recovery>

Cultures from the working cell bank were used to inoculate seed bottles containing a soy-based medium for cultivation. After reaching a target absorbance, the seed bottle was used to inoculate a fermentor containing the soy-based medium. Cultivation was performed at 34-38° C. and 120 rpm while maintaining pH at about 7.2 or higher using 3N NaOH. Sampling was performed every 2-3 hours to measure the absorbance. When the absorbance began to drastically increase, sampling was performed every 0.5-1 hour and absorbance was measured. Cultivation was terminated about 1 hour after the absorbance reached a certain value and remained constant. After termination of the cultivation, additional cultivation was performed without pH adjustment under the same temperature and rpm conditions until pH reached 5.5 or lower. After termination of the additional cultivation, sodium deoxycholate was added at a concentration of 0.12% to lyse cells. The lysate thus obtained was cooled to 10-15° C., and then incubated at the same temperature for about 3 hours without agitation to lead to protein precipitation. Subsequently, the resulting lysate was centrifuged to remove the precipitated proteins and cell debris.

<Purification>

The solution obtained by the centrifugation was filtered using a depth filter to remove proteins and cell debris which had not been settled during the centrifugation. The resulting filtrate was concentrated using a 100 kDa membrane, and then the resulting concentrated solution was subjected to ultrafiltration using 25 mM sodium phosphate buffer (pH 7.2). The ultrafiltration was performed until conductivity of the dialysate reached about 3-4 mS/cm, and transmembrane pressure (TMP) was set at 0.5-1.5 bar or less. Impurities were removed from the resulting solution, and cetrimonium bromide (Hexadecyl-trimethylammonium bromide (HB)) was added to the solution at a concentration of about 1.0 w/v %, followed by agitation for about 1 hour. Then, centrifugation was performed to precipitate polysaccharides. The pellet thus obtained was dissolved in about 0.25 M sodium chloride aqueous solution, and sodium iodide (NaI) was added thereto at a concentration of about 0.5 w/v %. This solution was centrifuged to recover the supernatant, and activated carbon was slowly added the resulting solution at a concentration of about 2.0 w/v % while agitating, followed by agitation for about 1 hour and filtration. The resulting filtrate was concentrated using a 30 kDa membrane, and then the concentrated solution was subjected to ultrafiltration using about 10 times volume of triple distilled water. The ultrafiltration was performed until conductivity of the dialysate reached about 10 μs/cm, and transmembrane pressure (TMP) was set at 0.5~1.5 bar or less. The resulting concentrated solution was subjected to sterile filtration, and stored frozen at −20° C. or lower.

The total protein content, total nucleic acid content, total polysaccharide content, and purification yield evaluated in each purification step are given in the following Tables 4 through 6.

TABLE 4

Protein content, nucleic acid content, and capsular polysaccharide recovery of serotype 3

| | Total protein content (mg) | Content ratio of protein to polysaccharide (%) | Total nucleic acid content (mg) | Content ratio of nucleic acid to polysaccharide (%) | Total polysaccharide content (mg) | Purification yield (%) |
| --- | --- | --- | --- | --- | --- | --- |
| Depth filter | 581320.00 | 354.46 | 27354.00 | 16.68 | 164000.00 | 100.00 |
| 100 KDa concentration/ ultrafiltration | 6829.00 | 5.57 | 601.60 | 0.49 | 122600.00 | 74.76 |
| CTAB/NaI | 7322.00 | 7.44 | 204.00 | 0.21 | 98400.00 | 60.00 |
| Activated carbon | 412.00 | 0.45 | 58.80 | 0.06 | 91600.00 | 55.85 |
| 30 KDa concentration/ ultrafiltration | 352.50 | 0.44 | 28.20 | 0.04 | 80400.00 | 49.30 |

TABLE 5

Protein content, nucleic acid content, and capsular polysaccharide recovery of serotype 6B

| | Total protein content (mg) | Content ratio of protein to polysaccharide (%) | Total nucleic acid content (mg) | Content ratio of nucleic acid to polysaccharide (%) | Total polysaccharide content (mg) | Purification yield (%) |
|---|---|---|---|---|---|---|
| Depth filter | 137280.00 | 65.37 | 4872.40 | 2.32 | 210000.00 | 100.00 |
| 100 KDa concentration/ultrafiltration | 8986.00 | 4.59 | 576.26 | 0.29 | 195800.00 | 93.24 |
| CTAB/NaI | 7030.00 | 4.30 | 352.06 | 0.22 | 163600.00 | 77.90 |
| Activated carbon | 1376.00 | 0.93 | 76.96 | 0.05 | 148400.00 | 70.67 |
| 30 KDa concentration/ultrafiltration | 843.00 | 0.70 | 43.23 | 0.04 | 120000.00 | 67.57 |

TABLE 6

Protein content, nucleic acid content, and capsular polysaccharide recovery of serotype 19A

| | Total protein content (mg) | Content ratio of protein to polysaccharide (%) | Total nucleic acid content (mg) | Content ratio of nucleic acid to polysaccharide (%) | Total polysaccharide content (mg) | Purification yield (%) |
|---|---|---|---|---|---|---|
| Depth filter | 1735640.00 | 2479.49 | 5053.30 | 7.22 | 70000.00 | 100.00 |
| 100 KDa concentration/ultrafiltration | 10288.00 | 16.87 | 252.56 | 0.41 | 61000.00 | 87.14 |
| CTAB/NaI | 5528.00 | 10.31 | 593.54 | 1.11 | 53600.00 | 76.57 |
| Activated carbon | 12.00 | 0.03 | 0.39 | ND[X] | 42400.00 | 60.57 |
| 30 KDa concentration/ultrafiltration | 8.00 | 0.02 | 0.06 | ND[X] | 44650.00 | 60.86 |

ND[X]: Not detected

The results of Tables 4 through 6 showed that capsular polysaccharides obtained by the production method according to the present invention satisfied a standard for residual protein content without any separate acidification process, and the recovery rates of capsular polysaccharides were also 49% or higher (serotype 3 capsular polysaccharide), 65% or higher (serotype 6B capsular polysaccharide), and 60% or higher (serotype 19A capsular polysaccharide), respectively. Therefore, the production method according to the present invention may be used to effectively produce capsular polysaccharides by the simplified process.

Example 2. Production of Capsular Polysaccharides of Pneumococcal Serotypes 7F and 14

<Preparation of Cell Bank>

Respective seed stocks producing pneumococcal serotypes 7F and 14 were obtained from American Type Culture Collection [ATCC]. Strains used in seed culture and main culture are given in the following Table 7.

TABLE 7

| Serotype | ATCC No. |
|---|---|
| 7F | 10351 |
| 14 | 6314 |

Several generations of seed stocks were created (generations F1, F2, and F3). Two additional generations of seed stocks were produced. The first additional generation was cultured from an F3 vial, and the subsequent generation was cultured from a vial of the first additional generation. Seed vials were stored frozen (←−70° C.) with synthetic glycerol as a cryopreservative. For cell bank preparation, all cultures were grown in a soy-based medium. Prior to freezing, cells were concentrated by centrifugation, spent medium was removed, and cell pellets were re-suspended in fresh medium containing a cryopreservative (e.g., synthetic glycerol).

<Culture and Recovery>

Cultures from the working cell bank were used to inoculate seed bottles containing a soy-based medium for cultivation. After reaching a target absorbance, the seed bottle was used to inoculate a fermentor containing the soy-based medium. Cultivation was performed at 34-38° C. and 120 rpm while maintaining pH at about 7.2 or higher using 3N NaOH. Sampling was performed every 2-3 hours to measure the absorbance. When the absorbance began to drastically increase, sampling was performed every 0.5~1 hours to measure the absorbance. Cultivation was terminated about 1 hour after the absorbance reached a certain value and remained constant. After termination of the cultivation, additional cultivation was performed without pH adjustment under the same temperature and rpm conditions until pH reached 5.5 or lower. After termination of the additional cultivation, sodium deoxycholate was added at a concentration of 0.12% to lyse cells. The lysates thus obtained were cooled to 10~15° C., and then incubated at the same temperature for about 3 hours without agitation to lead to protein precipitation. Subsequently, the resulting lysate was centrifuged to remove the precipitated proteins and cell debris.

<Purification>

The solution obtained by the centrifugation was filtered using a depth filter to remove proteins and cell debris which had not been settled during the centrifugation. The resulting filtrate was concentrated using a 100 kDa membrane, and then the resulting concentrated solution was subjected to ultrafiltration using 25 mM sodium phosphate buffer (pH 7.2). The ultrafiltration was performed until conductivity of the dialysate reached about 3-4 mS/cm, and transmembrane pressure (TMP) was set at 0.5-1.5 bar or less. Impurities were removed from the resulting solution, and cetrimonium bromide (Hexadecyl-trimethylammonium bromide (HB)) was added at a concentration of about 1.0 w/v % followed by agitation for about 1 hour and centrifugation to recover the supernatant. Then, sodium iodide (NaI) was added to the supernatant at a concentration of about 0.5 w/v %. The obtained solution was centrifuged to recover the supernatant, and activated carbon was slowly added to the obtained solution at a concentration of about 2.0 w/v % while agitating, followed by agitation for about 1 hour and filtration. The resulting filtrate was concentrated using a 30 kDa membrane, and then the concentrated solution was subjected to ultrafiltration using about 10 times volume of triple distilled water. The ultrafiltration was performed until conductivity of the dialysate reached about 10 μs/cm, and transmembrane pressure (TMP) was set at 0.5-1.5 bar or less. The resulting concentrated solution was subjected to sterile filtration, and stored frozen at −20° C. or lower.

Total protein content, total nucleic acid content, total polysaccharide content, and purification yield evaluated in each purification step are given in the following Tables 8 through 9.

The results of Tables 8 and 9 showed that capsular polysaccharides obtained by the production method according to the present invention satisfied a standard for residual protein content without any separate acidification process, and the recovery rates of capsular polysaccharides were also 60% or higher (serotype 7F capsular polysaccharide) and 55% or higher (serotype 14 capsular polysaccharide), respectively. Therefore, the production method according to the present invention may be used to effectively produce capsular polysaccharides by the simplified process.

Example 3. Production of Capsular Polysaccharides of Pneumococcal Serotype 23F

<Preparation of Cell Bank>

A seed stock producing pneumococcal serotype 23F was obtained from American Type Culture Collection [ATCC, No. 6323]. Several generations of seed stocks were created (generations F1, F2, and F3). Two additional generations of seed stocks were produced. The first additional generation was cultured from an F3 vial, and the subsequent generation was cultured from a vial of the first additional generation. Seed vials were stored frozen (←−70° C.) with synthetic glycerol as a cryopreservative. For cell bank preparation, all cultures were grown in a soy-based medium. Prior to freezing, cells were concentrated by centrifugation, spent medium was removed, and cell pellets were re-suspended in fresh medium containing a cryopreservative (e.g., synthetic glycerol).

TABLE 8

Protein content, nucleic acid content, and capsular polysaccharide recovery of serotype 7F

| | Total protein content (mg) | Content ratio of protein to polysaccharide (%) | Total nucleic acid content (mg) | Content ratio of nucleic acid to polysaccharide (%) | Total polysaccharide content (mg) | Purification yield (%) |
|---|---|---|---|---|---|---|
| Depth filter | 1861130.00 | 1604.42 | 4325.00 | 3.73 | 116000.00 | 100.00 |
| 100 KDa concentration/ ultrafiltration | 21352.00 | 21.39 | 546.80 | 0.55 | 99800.00 | 86.03 |
| CTAB/NaI | 5962.00 | 6.47 | 565.70 | 0.61 | 92200.00 | 79.48 |
| Activated carbon | 428.00 | 0.50 | 269.67 | 0.32 | 85200.00 | 73.45 |
| 30 KDa concentration/ ultrafiltration | 259.00 | 0.42 | 21.30 | 0.03 | 61300.00 | 60.26 |

TABLE 9

Protein content, nucleic acid content, and capsular polysaccharide recovery of serotype 14

| | Total protein content (mg) | Content ratio of protein to polysaccharide (%) | Total nucleic acid content (mg) | Content ratio of nucleic acid to polysaccharide (%) | Total polysaccharide content (mg) | Purification yield (%) |
|---|---|---|---|---|---|---|
| Depth filter | 138480.00 | 121.47 | 6609.40 | 5.80 | 114000.00 | 100.00 |
| 100 KDa concentration/ ultrafiltration | 10624.00 | 12.92 | 1369.61 | 1.67 | 82200.00 | 72.11 |
| CTAB/NaI | 3706.00 | 4.10 | 491.22 | 0.54 | 90400.00 | 79.30 |
| Activated carbon | 656.00 | 0.99 | 274.56 | 0.42 | 66000.00 | 57.89 |
| 30 KDa concentration/ ultrafiltration | 209.00 | 0.41 | 68.09 | 0.13 | 50490.00 | 55.87 |

<Culture and Recovery>

Culture from the working cell bank was used to inoculate a seed bottle containing a soy-based medium for cultivation. After reaching a target absorbance, the seed bottle was used to inoculate a fermentor containing the soy-based medium. Cultivation was performed at 34-38° C. and 120 rpm while maintaining pH at about 7.2 or higher using 3N NaOH. Sampling was performed every 2-3 hours to measure the absorbance. When the absorbance began to drastically increase, sampling was performed every 0.5-1 hours to measure the absorbance. Cultivation was terminated about 1 hour after the absorbance reached a certain value and remained constant. After termination of the cultivation, additional cultivation was performed without pH adjustment under the same temperature and rpm conditions until pH reached 5.5 or lower. After termination of the additional cultivation, sodium deoxycholate was added at a concentration of 0.12% to lyse cells. The lysate thus obtained was cooled to 10~15° C., and then incubated at the same temperature for about 3 hours without agitation to lead to protein precipitation. Subsequently, the resulting lysate was centrifuged to remove the precipitated proteins and cell debris.

<Purification>

The solution obtained by the centrifugation was filtered using a depth filter to remove proteins and cell debris which has not been settled during the centrifugation. The resulting filtrate was concentrated using a 100 kDa membrane, and then the resulting concentrated solution was subjected to ultrafiltration using 25 mM sodium phosphate buffer (pH 7.2). The ultrafiltration was performed until conductivity of the dialysate reached about 3~4 mS/cm, and transmembrane pressure (TMP) was set at 0.5~1.5 bar or less. Impurities were removed from the resulting solution, and cetrimonium bromide (Hexadecyl-trimethylammonium bromide (HB)) was added at a concentration of about 2.5 w/v % followed by agitation for about 1 hour and centrifugation to precipitate polysaccharides. The pellet thus obtained was dissolved in about 0.25 M sodium chloride aqueous solution, and sodium iodide (NaI) was added thereto at a concentration of about 0.5 w/v %. This solution was centrifuged to recover a supernatant, and activated carbon was slowly added to the resulting solution at a concentration of about 2.0 w/v % while agitating, followed by agitation for about 1 hour and filtration. The resulting filtrate was concentrated using a 30 kDa membrane, and then the concentrated solution was subjected to ultrafiltration using about 10 times volume of triple distilled water. The ultrafiltration was performed until conductivity of the dialysate reached about 10 μs/cm, and transmembrane pressure (TMP) was set at 0.5~1.5 bar or less. The resulting concentrated solution was subjected to sterile filtration, and stored frozen at −20° C. or lower.

TABLE 10

Protein content, nucleic acid content, and capsular polysaccharide recovery of serotype 23F

|  | Total protein content (mg) | Content ratio of protein to polysaccharide (%) | Total nucleic acid content (mg) | Content ratio of nucleic acid to polysaccharide (%) | Total polysaccharide content (mg) | Purification yield (%) |
| --- | --- | --- | --- | --- | --- | --- |
| Depth filter | 1667780.00 | 1437.74 | 5740.00 | 4.95 | 116000.00 | 100.00 |
| 100 KDa concentration/ ultrafiltration | 17798.00 | 17.28 | 442.90 | 0.43 | 103000.00 | 88.79 |
| CTAB/NaI | 7678.00 | 9.23 | 299.00 | 0.36 | 83200.00 | 71.72 |
| Activated carbon | ND* | ND* | 137.20 | 0.18 | 77600.00 | 66.90 |
| 30 KDa concentration/ ultrafiltration | ND* | ND* | 5.605 | 0.01 | 55860.00 | 64.53 |

Total protein content, total nucleic acid content, total polysaccharide content, and purification yield evaluated in each purification step are given in the following Table 10.
ND*: Not detected The results in Table 10 showed that the serotype 23F capsular polysaccharide obtained by the production method according to the present invention satisfied a standard for residual protein content without employment of an additional acidification process, and the recovery rate of capsular polysaccharide was also 60% or higher. Therefore, the production method according to the present invention may be used to effectively produce capsular polysaccharides by the simplified process.

The invention claimed is:

1. A method of producing a capsular polysaccharide having a pneumococcal serotype, the method comprising:
    (a) cultivating bacterial cells that produce a pneumococcal serotype while maintaining pH of a culture broth in the range of 7.0 to 9.4;
    (b) terminating the cultivating of step (a) at a time between when the absorbance of the culture broth remains constant and when the absorbance begins to decrease;
    (c) performing additional cultivating of the culture broth of step (b) without addition of a pH adjuster until the pH of the culture broth reaches pH of 5.5 or lower;
    (d) adding a lysing agent to the culture broth obtained from step (c) to lyse cells, precipitating proteins, and removing the precipitated proteins and cell debris to obtain a clarified cell lysate; and
    (e) isolating and purifying the capsular polysaccharide from the lysate obtained from step (d).

2. The method of claim 1, wherein the pneuomococcal serotype is 1, 2, 3, 4, 5, 6A, 6B, 7F, 9N, 9V, 14, 18C, 19A, 19F, 22F, 23F or 33F.

3. The method of claim 1, wherein the cultivating of step (a) is performed at 34-38° C. under agitation at 50-150 rpm.

4. The method of claim 1, wherein step (b) is performed by terminating the cultivating of step (a) within 1 to 3 hours from the time when the absorbance of the culture broth remains constant.

5. The method of claim 1, wherein the additional cultivating of step (c) is performed at 34-38° C. under agitation at 50-150 rpm without pH adjustment.

6. The method of claim 1, wherein the lysing agent used in step (d) is sodium deoxycholate.

7. The method of claim 1, wherein step (d) is performed by adding the lysing agent to the culture broth obtained from step (c) to lyse cells, then incubating the resulting cell lysate at 10-20° C. for 3-24 hours without agitation to precipitate proteins, and removing the precipitated proteins and cell debris by centrifugation.

8. The method of claim 1, wherein the isolating and purifying of step (e) comprises:
   (i) filtering the lysate obtained from step (d) using a depth filter;
   (ii) concentrating a filtrate obtained from step (i), followed by ultrafiltration and centrifugation;
   (iii) reacting a supernatant obtained from step (ii) with a cationic surfactant, and then centrifuging the resulting solution to obtain a pellet or supernatant containing capsular polysaccharides;
   (iv) reacting the capsular polysaccharides obtained from step (iii) with sodium iodide, followed by centrifugation, thereby obtaining a supernatant;
   (v) adding activated carbon to the solution obtained from step (iv), followed by filtration; and
   (vi) concentrating a filtrate obtained from step (v), followed by ultrafiltration and centrifugation, thereby obtaining capsular polysaccharides.

9. The method of claim 8, wherein the concentrating of step (ii) is performed using a 100 kDa membrane.

10. The method of claim 8, wherein the concentrating of step (iv) is performed using a 30 kDa membrane.

11. The method of claim 8, wherein the cationic surfactant used in step (iii) is cetyltrimethylammonium bromide.

12. The method of claim 11, wherein the cetyltrimethylammonium bromide is used at a concentration of 0.5~3.0%.

13. The method of claim 8, wherein the activated carbon used in step (v) used at a concentration of 1-5% (w/v).

* * * * *